US006458108B1

(12) United States Patent
Tangri

(10) Patent No.: US 6,458,108 B1
(45) Date of Patent: Oct. 1, 2002

(54) HANDHELD EYE WASHING APPARATUS

(76) Inventor: Kuldip Chand Tangri, 8044 N Harding Ave., Skokie, IL (US) 60076

(*) Notice: Subject to any disclaimer, the term of this patent is extended or adjusted under 35 U.S.C. 154(b) by 0 days.

(21) Appl. No.: 09/574,944

(22) Filed: May 19, 2000

Related U.S. Application Data

(60) Provisional application No. 60/176,657, filed on Jan. 18, 2000, and provisional application No. 60/177,584, filed on Jan. 22, 2000.

(51) Int. Cl.$^{7}$ .............................................. A61M 35/00

(52) U.S. Cl. ....................... 604/295; 604/294; 604/300; 604/301

(58) Field of Search ......................... 604/289, 294–302; 128/200.23, 200.24; 222/527, 533, 556; 4/625

(56) References Cited

U.S. PATENT DOCUMENTS

| | | | | |
|---|---|---|---|---|
| 4,531,944 A | | 7/1985 | Bechtle | |
| 4,616,783 A | | 10/1986 | Weber et al. | |
| 4,641,384 A | | 2/1987 | Landsberger et al. | |
| 4,685,906 A | | 8/1987 | Murphy | |
| 4,758,237 A | * | 7/1988 | Sacks | 604/289 |
| 4,792,334 A | | 12/1988 | Py | |
| 5,020,526 A | | 6/1991 | Epstein | |
| 5,152,435 A | | 10/1992 | Stand et al. | |
| 5,201,726 A | | 4/1993 | Kirkham | |
| 5,346,132 A | | 9/1994 | Hahn et al. | |
| 5,401,259 A | | 3/1995 | Py | |
| 5,588,564 A | | 12/1996 | Hutson et al. | |
| 5,607,410 A | | 3/1997 | Branch | |
| 5,893,515 A | | 4/1999 | Hahn et al. | |

* cited by examiner

*Primary Examiner*—Kim M. Lewis

(57) ABSTRACT

This is a handheld eye flushing apparatus that comprises an eyecup that holds eyewash liquid in it for eye flushing. The rim of the eyecup is contoured to the eye orbit and rests on the eye orbital area. Attached to the inside of the eyecup is a stirring mechanism that stirs the eyewash liquid during usage. The force and the duration of the stirring is predetermined to prevent eye damage. This apparatus accommodates the free movement of the eyelids and the eyeball inside of the eyecup during utilization. The rim of this eyecup may have a liner to further increase comfort and liquid sealing around the eye. An magnetic strip may be placed near the bottom part of the rim to catch ferrous metal particles in industrial environment usage. An grid may be added between the rim and the agitator to keep the user away from the agitator.

45 Claims, 1 Drawing Sheet

HANDHELD EYE WASHING APPARATUS

This application claims the benefit of provisional applications No. 60/176,657 filed on Jan. 18, 2000 and No. 60/177,584 filed on Jan. 22, 2000.

FIELD OF THE INVENTION

This invention relates to the maintenance and hygiene of the eye, specifically washing proteins, eyelash and foreign objects from the eye.

BACKGROUND OF THE INVENTION

Nature made eyes self-cleaning and lubricating. Sometimes due to unexplainable reasons or with aging it ceases to provide adequate tear flow which in turn causes the eyes to feel crusty and tired. A satisfactory hygienic apparatus for eye washing is not readily available in the marketplace at the present time. There are numerous apparatuses existing, which can wash proteins from contact lenses for the eyes, but there is nothing currently available to wash the proteins from the actual eyes. The few eyecups, which do exist in the marketplace, are quite ineffective. U.S. Pat. No. 4,758,237 issued to Mr. Herman Sacks is relevant. In this patent Mr. Sacks tried to achieve an effective eye washer design but the design is inadequate. Starting with his eyecup, it does not cover enough of the area around the eye and it may be expensive to make. There are unfavorable possibilities of focusing the eyewash liquid towards the eye improperly and damage to the eyeball from the pressure build up in chamber 3 if filter 8 is clogged. Further disadvantages, such as eyewash liquid contamination, high quantity of eyewash liquid utilization due to separate sump for the eyewash liquid and a pump, exist. Unlike Mr. Sacks's device, the present invention covers all of the eye and area around the eye. It is very inexpensive to make, it is adaptable due to its size, and there are no known flaws and no liquid lines from the pump. Also, there is no sump, sump pump, nor filter.

SUMMARY OF THE INVENTION

In this invention, an eyecup has a stirring mechanism to stir the eyewash liquid inside. The eyecup has an appropriate opening with an appropriate width rim contoured to fit the eye orbital and ample room for the eyelids and eyeball movement. Its rim is wider to accommodate the orbital variation and to get a better seal and comfort around the eye. Further, an optional soft-liner may be added to the rim. The stirring mechanism consists of an agitator and a driver for the agitator. The agitator is inside and the driver and its operating necessities are outside the eyecup. This device has a universal rim but because the contour of the left and right eyes is different, it may be made contoured to the left and right eye individually or jointly for both eyes. This is not shown in the diagrams because it is self-explanatory, and may be achieved with no problem. To make the present invention compact, components of the Handheld Eye Washing Apparatus may be laid out differently and an eyewash liquid warmer may be added to this apparatus.

The object of this invention is to provide a handy, portable and an inexpensive hygiene-aiding apparatus for the eye. It provides an effective flow of eyewash liquid to flush out the proteins and foreign objects from the eye and it is a boon for contact lens wearers.

DETAILED DESCRIPTION OF DRAWINGS

Figure 1:
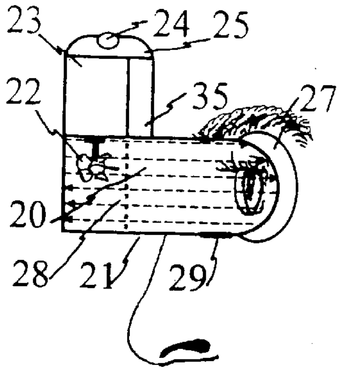
FIG. 1 is a side elevation view of the present invention, applied to the eye.

FIG. 1 is a side view of the apparatus that shows how it may be used. It is a one-piece molded throwaway type where a user uses it a certain number of times and throws it away like a toothbrush. In this figure, the user fills the eyecup 21 with eyewash liquid 20 and places it on the eye orbital area by tilting the head forward and bringing the head straight up. The momentary switch 24 is then pushed to activate the driver 23, which is an electrical motor where the driver is connected to the agitator 22 that turns inside of the eyecup 21, stirring or churning the eyewash liquid vigorously. Momentary switch 24 has an internal circuitry to stop the apparatus after a predetermined time. The driver 23 will stop even if the switch 24 is held on. To restart the driver 23 the momentary switch 24 must be released and pushed again. After the user is done with this procedure, he/she will take the eyecup 21 off by tilting his/her head forward, empty it to put it away after cleaning or refill it to repeat the process, if necessary. A housing 25 holds the driver 23, the power source and the momentary switch 24 for the driver 23. 35 is an access panel to the power source, such as a battery, for the driver 23 in the housing 25. Rim 27 of the eyecup 21 is contoured to fit the eye orbit. Grill 28 keeps the user away from the agitator 22. Magnetic strip 29 is molded into the eyecup 21 closer to the bottom part of the rim 27. If it is used as a first aid apparatus in an industrial environment, during the utilization procedure, magnetic strip 29 will attract ferrous metal particles. Dotted lines and arrows 20 show eyewash liquid movement inside the eyecup 21.

Figure 2:
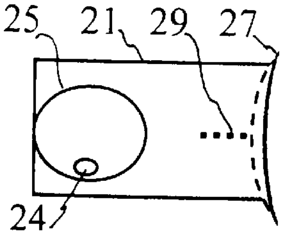
FIG. 2 is a top view of the apparatus.

FIG. 2 is the top view of the apparatus. It shows the eyecup 21, a momentary switch 24, housing 25 for the driver 23, the power source, and rim 27. Magnetic strip 29 is shown as the dotted line.

Figure 3:
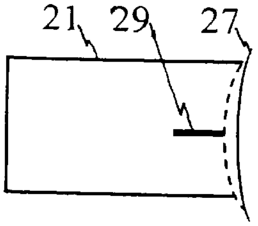
FIG. 3 is a bottom view of the apparatus.

FIG. 3 is a bottom view of the apparatus. It shows the eyecup 21, rim 27, and magnetic strip 29.

Figure 4:
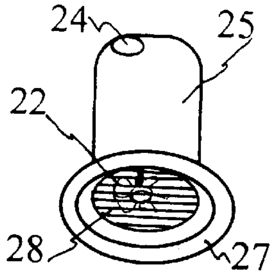
FIG. 4 is a frontal view or view from the rim of the apparatus.

FIG. 4 is a front view of the apparatus. It shows the rim 27 and through this rim 27, a grill 28; located further in is an agitator 22 and outside is the housing 25 to hold the driver 23 and required components for the driver 23. 24 is a momentary pushbutton switch.

Figure 5:
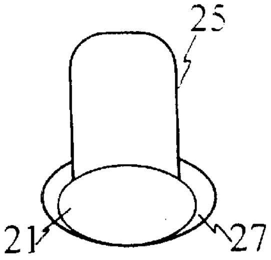
FIG. 5 is a rear view of the apparatus.

FIG. 5 is a rear view of the apparatus showing eyecup 21, rim 27 and housing 25 for the driver 23 and the required components for the driver 23.

Figure 6:
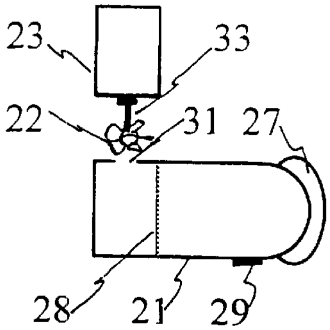
FIGS. 6, 7, and 8 illustrate disassembled apparatuses that show the assembly achievement of the agitator in different situations.

FIG. 6 shows the detached driver 23 from the eyecup 21 with the agitator 22 mounted on its shaft 33. In this embodiment, the shaft side of the driver 23 is watertight. When it is assembled, a portion of the driver 23 is press fitted into the opening 31 of the eyecup 21. Rim 27, grid 28, and magnetic strip 29 are shown in FIG. 6.

Figure 7:
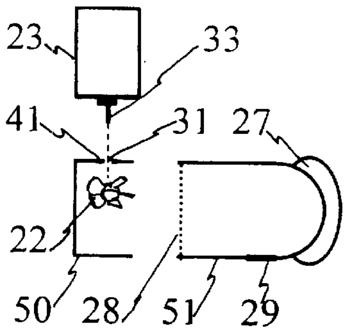

FIG. 7 shows the eyecup is detachable into two parts, where 51 is the front portion and 50 is the rear portion. This embodiment shows shaft 33 of the driver 23 is detached from the agitator 22, where the agitator 22 stays inside the rear portion of the eyecup 50. Seal 41 is shown mounted in opening 31. When it is assembled, the shaft 33 of the driver 23 enters through seal 41 to avoid the eyewash liquid leakage around it. As in previous figures, 27 is a rim, 28 is a grill, and 29 is magnetic strip. It is shown assembled in FIG. 9.

Figure 8:
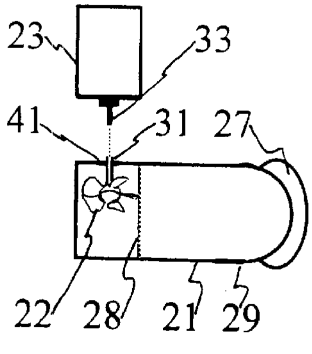

FIG. 8 is similar to FIG. 7 except the eyecup 21 does not come apart and the agitator 22 has an extended hollow shaft, extending out through seal 41 where seal 41 is mounted in the opening 31 of eyecup 21. When it is assembled, shaft 33 of driver 23 enters the hollow shaft of the agitator 22. This embodiment of the apparatus is used to make internal parts of the apparatus corrosion resistive where the agitator is made of corrosion resistive material and is shown assembled in FIG. 9.

Figure 9:
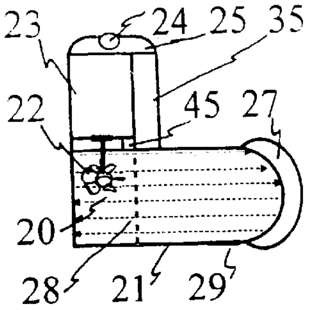
FIG. 9 is an assembled device of the embodiments shown in FIG. 7 and FIG. 8.

FIG. 9 is similar to FIG. 1 except in this figure, opening 45 is added. Opening 45 in the housing 25 is placed between the driver 23 and the eyecup 21 to drain eyewash liquid accumulation in case the seal 41 leaks. This seal 41 is shown in FIG. 7 and FIG. 8. FIG. 9 is an assembled embodiment of FIG. 7 and FIG. 8, where 20 is eyewash liquid in the eyecup 21. Agitator 22 is mounted on the shaft of driver 23. FIG. 9 shows momentary switch 24, housing 25, and access door 35. 27, 28, and 29 are the rim, grill, and magnetic strip, respectively.

Figure 10:
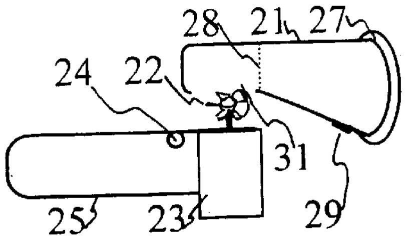
FIG. 10 shows another embodiment that is laid out differently and the outlook of the eyecup is different.

FIG. 10 is another embodiment of the apparatus where housing 25 for the driver 23, the power source and the momentary switch 24 for the driver 23 are laid out differently. The eyecup 21 is shaped differently and is detachable from the housing 25. 31 is an opening of the eyecup 21. Agitator 22 stays on the driver 23. Although it is not shown, the housing 25 may have a switching mechanism that will not to let the driver operate unless the eyecup 21 is attached to it. All other numbers correspond to the embodiment of FIG. 1.

Figure 11:
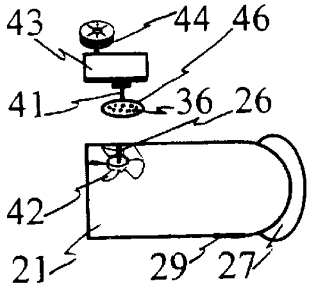
FIG. 11 shows a hand-operated driver and magnetic coupling between agitator and driver where the agitator is ferrous metal impregnated.

FIG. 11 has a hand-operated driver 43 instead of an electric motor as shown in the previous embodiments. Driver 43 is an arrangement of gears that achieve the proper speed where a thumb wheel 44 is used to operate the driver 43. Instead of a thumb wheel, a hand crank or a spring-loaded hand winding mechanism may be used. This embodiment may also use a magnetic coupling to transfer the power from the driver 43 to the agitator 42. Here, the disc 46 is impregnated with magnetic segments 36 and it is installed on the shaft 41 of the driver 43. Further, the disc 46 is aligned with agitator 42 to form the magnetic coupling that transfers the power from driver 43 to agitator 42. Agitator 42 may be made of ferrous metal or impregnated with ferrous metal and can be impregnated with magnetic segments to match the disc 46 as well. This embodiment has no opening in the wall of eyecup 21 or a direct coupling between disc 46 and agitator 42 except magnetic force. Axle 26 of the agitator 42 is attached to the wall of the eyecup 21. FIG. 11 also shows the magnetic impregnation 36. When the device is assembled, the magnetic force creates a coupling between agitator 42 and disc 46 and driver 43 turns the disc 46 and agitator 42 inside the eyecup 21. As in previous figures, FIG. 11 shows rim 27 and magnetic strip 29. The remaining assembly may be similar to FIG. 1.

Figure 12:
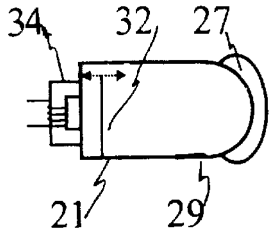
FIG. 12 shows an electromagnet driver and a ferrous metal impregnated straight blade agitator mounted inside the eyecup.

FIG. 12 has an entirely different agitator and driver. Agitator 32 is a straight blade impregnated with ferrous metal mounted inside the eyecup 21 to stir the eyewash liquid. A driver 34, comprising an electromagnet with an oscillator to control its energizing frequency is placed outside of the eyecup 21. When driver 34 is energized, it pulls the agitator 32 towards it and when it is de-energized, it releases the agitator 32 to its original position, thereby causing the agitator 32 to move back and forth. This movement creates agitation in the eyecup 21 and to the eyewash liquid 20 inside of the eyecup 21. The oscillator is not shown in the diagram because it is well-known art. The rest of the powering, controlling and housing systems for this driver may be similar to the embodiment in FIG. 1.

Figure 13:
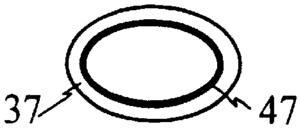
FIG. 13 shows a detachable adapter rim.
Figure 14:
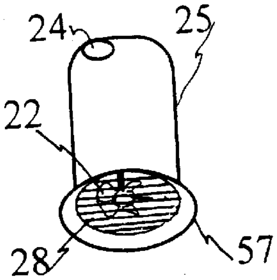
FIG. 14 shows an eyecup having a rim onto which a detachable adapter rim may attach.

FIG. 13 shows a detachable adapter rim 37 with a groove 47 to fit on the rim of a straight rim eyecup shown in FIG. 14. This detachable adapter rim 37 may be used on previously known eyecups or manufacturing conveniences.

FIG. 14 shows an eyecup having a straight rim 57, The groove 47 of the detachable adapter rim 37 shown in FIG. 13 fits onto rim 57. The remaining numbers correspond to the embodiment in FIG. 1.

Although the present invention has been described with reference to preferred embodiments, numerous modifications and variations can be made and still the result will come within the scope of the invention. No limitation with respect to the specific embodiments disclosed herein is intended or should be inferred.

All figures illustrate eyecup 21.

Opening 31 is an opening of the driver and the agitator. Seal 41 is used to avoid eyewash liquid leakage if the embodiments shown in FIG. 7 and FIG. 8 are applied.

22, 32 and 42 are different types of agitators. 42 is an agitator impregnated with ferrous metal and 32 is a straight blade type agitator also impregnated with ferrous metal.

23, 34 and 43 are three different types of drivers of the agitators where 23 is an electrical motor, 34 is an electromagnet mounted outside the eyecup and 43 is a thumb wheel or hand-operated. 33 is a shaft of the driver 23, 41 is a shaft of 43.

The momentary switch 24 that turns the driver has special circuitry to shut the driver off after a predetermined time. 44 is a thumb wheel that powers the driver.

Housing 25 holds the driver and its power and control source. 35 is an access door for the power source. Opening 45 in the housing drains liquid to avoid accumulation of eyewash liquid between the driver and the eyecup.

Magnetic segment impregnated disc 46 makes a magnetic coupling; 26 is an axle and 36 is the magnetic impregnation.

Rim 27 is contoured to fit the eye orbital area. Detachable adapter rim 37 and groove 47 fit onto the straight rim 57 of the eyecup 21.

Grill 28 keeps the user away from the agitator 22.

Magnetic strip 29 attracts the ferrous metal particles during the eye washing procedure.

Dotted lines and arrows 20 show the eye wash liquid inside of the eyecup.

As I claimed:

1. A handheld eye washer comprising:

an eyecup capable of holding a cleansing fluid;

an agitator in the eyecup to agitate the fluid against an eye corneal surface; and a magnetic strip in the eyecup for catching metal particles during eye washing;

said eyecup having a proximal end with a rim shaped to fit around an eye socket.

2. The eye wash of claim 1, wherein the agitator further comprises an electric motor, an impeller, and a power source mounted to the eyecup.

3. The eye wash of claim 2 further comprising a momentary switch.

4. The eye wash of claim 2 further comprising a housing attached to the eyecup, said housing having a watertight wall adjacent to the eyecup and having the agitator mounted therein.

5. The eye wash of claim 4, wherein the housing further comprises a removable panel.

6. The eye wash of claim 4, wherein the housing is mounted at about a right angle from the eyecup.

7. The eye wash of claim 6, wherein the housing further comprises a separable body to access the agitator.

8. The eye wash of claim 4, wherein the housing is mounted distally from the rim.

9. The eye wash of claim 4, wherein the housing further comprises an opening to ambient to drain cleansing fluid therefrom.

10. The eye wash of claim 2, wherein the eyecup further comprises at least two separable members, and one of said members houses the agitator.

11. The eye wash of claim 10 further comprising a housing attached to the member housing the agitator, said housing having a watertight wall adjacent to the eyecup.

12. The eye wash of claim 1, wherein the agitator further comprises a hand-operated driver mechanism.

13. The eye wash of claim 1, wherein the agitator further comprises an oscillating rod.

14. The eye wash of claim 1 further comprising a grill in the eyecup.

15. The eye wash of claim 1 further comprising a magnetic element affixed to the eyecup.

16. The eye wash of claim 1, wherein the rim further comprises an adapter rim removably attached to the rim.

17. The eye wash of claim 16, wherein the adapter rim further comprises a mounting mechanism for attaching to the rim.

18. The eye wash of claim 17, wherein the mounting mechanism further comprises a mounting groove for attaching to the rim.

19. A handheld eye washer comprising:

an eyecup capable of holding a cleansing fluid;

said eyecup further having a magnetic strip therein for catching metal particles during eye washing;

an agitator in the eyecup to agitate the fluid against an eye corneal surface;

said eyecup having a proximal end with a rim shaped to fit around an eye socket;

a housing mounted at right angles to the eyecup and distally from the rim;

said housing providing a mount for an agitator driver; and wherein an agitator impeller is located in the eyecup.

20. The eye wash of claim 19, wherein the housing further comprises a watertight wall adjacent to the eyecup having the agitator mounted therein.

21. The eye wash of claim 19, wherein the agitator further comprises an electric motor, an impeller, and a power source mounted to the eyecup.

22. The eye wash of claim 21 further comprising a momentary switch.

23. The eye wash of claim 19, wherein the agitator further comprises a hand-operated driver mechanism.

24. The eye wash of claim 19, wherein the agitator further comprises an oscillating rod.

25. The eye wash of claim 19 further comprising a grill in the eyecup.

26. The eye wash of claim 19, wherein the housing further comprises a removable panel.

27. The eye wash of claim 19, wherein the housing further comprises a separable body to access the agitator.

28. The eye wash of claim 19, wherein the eyecup further comprises at least two separable members, and one of said members houses the agitator.

29. The eye wash of claim 19, wherein the housing further comprises an opening to ambient to drain cleansing fluid therefrom.

30. The eye wash of claim 19, wherein the rim further comprises an adapter rim removably attached to the rim.

31. The eye wash of claim 30, wherein the adapter rim further comprises a mounting mechanism for attaching to the rim.

32. The eye wash of claim 31, wherein the mounting mechanism further comprises a mounting groove for attaching to the rim.

33. A handheld eye washer comprising:

an eyecup capable of holding a cleansing fluid, and having a longitudinal axis;

said eyecup having a proximal end with a rim shaped to fit around an eye socket;

said eyecup further having a magnetic strip therein for catching metal particles during eye washing;

a housing having its longitudinal axis mounted parallel to the eyecup's longitudinal axis;

said housing providing a mount for a agitator driver; and an impeller in the eyecup to agitate the fluid against an eye corneal surface.

34. The eye wash of claim 33, wherein the housing houses an electric motor, and a power source.

35. The eye wash of claim 33, wherein the eyecup further comprises an opening to mount the impeller therethrough.

36. The eye wash of claim 33, wherein the housing further comprises a separable body to access the eyecup.

37. The eye wash of claim 36, wherein the housing further comprises a lock-out mechanism to prevent operation when the housing is separated from the eyecup.

38. A handheld eye washer comprising:

an eyecup capable of holding a cleansing fluid;

said eyecup having a proximal end with a rim shaped to fit around an eye socket;

said eyecup further having a magnetic strip therein cup for catching metal particles during eye washing;

a housing mounted to the eyecup and distally from the rim;

said housing providing a mount for a hand-operated driver mechanism for an impeller; and said impeller mounted in the eyecup to agitate the fluid against an eye corneal surface.

39. The eye wash of claim 38, wherein the housing further comprises a gear set and a hand-operated power source.

40. The eye wash of claim 38, wherein the housing further comprises a magnetic coupling to transfer power to the impeller.

41. The eye wash of claim 38, wherein the housing mounts to a rear end of the eyecup.

42. A handheld eye washer comprising:

an eyecup capable of holding a cleansing fluid;

said eyecup having a proximal end with a rim shaped to fit around an eye socket;

said eyecup further having a magnetic strip therein cup for catching metal particles during eye washing;

a housing mounted to the eyecup and distally from the rim;

said housing providing a mount for an electromagnet driver mechanism; and an impeller in the eyecup to agitate the fluid against an eye corneal surface.

43. The eye wash of claim 42, wherein the housing houses the impeller and a power source.

44. The eye wash of claim 43, wherein the impeller further comprises an oscillating rod.

45. The eye wash of claim 42, wherein the housing is mounted at a rear end of the eyecup.

* * * * *